United States Patent
Shvetsov et al.

(10) Patent No.: US 12,186,005 B2
(45) Date of Patent: Jan. 7, 2025

(54) FILTERING METHOD AND APPARATUS

(71) Applicant: Buffalo Filter LLC, Lancaster, NY (US)

(72) Inventors: Kyrylo Shvetsov, Depew, NY (US); Gregory Pepe, Lancaster, NY (US); Samantha Bonano, Williamsville, NY (US); Michael Miller, Depew, NY (US)

( * ) Notice: Subject to any disclaimer, the term of this patent is extended or adjusted under 35 U.S.C. 154(b) by 1013 days.

(21) Appl. No.: 16/968,316

(22) PCT Filed: Nov. 21, 2019

(86) PCT No.: PCT/US2019/062677
§ 371 (c)(1),
(2) Date: Aug. 7, 2020

(87) PCT Pub. No.: WO2020/106993
PCT Pub. Date: May 28, 2020

(65) Prior Publication Data
US 2021/0077177 A1    Mar. 18, 2021

Related U.S. Application Data

(60) Provisional application No. 62/770,270, filed on Nov. 21, 2018.

(51) Int. Cl.
*A61B 18/14*    (2006.01)
*A61B 18/00*    (2006.01)
(Continued)

(52) U.S. Cl.
CPC ....... *A61B 18/1402* (2013.01); *B01J 20/0233* (2013.01); *B01J 20/20* (2013.01);
(Continued)

(58) Field of Classification Search
CPC .................. A61B 2218/006; A61B 2218/008
See application file for complete search history.

(56) References Cited

U.S. PATENT DOCUMENTS 5,160,334 A  *  11/1992 Billings ................ A61B 18/14
                                                                606/49
5,234,428 A      8/1993 Kaufman
(Continued)

FOREIGN PATENT DOCUMENTS

CA    2187467 A1    8/1997
CA    2530962 A1    1/2005
(Continued)

OTHER PUBLICATIONS

International Search Report for PCT/US2019/062677, completed on Mar. 16, 2020, mailed Mar. 30, 2020.

*Primary Examiner* — Ronald Hupczey, Jr.
(74) *Attorney, Agent, or Firm* — Timothy W. Menasco, Esq.; Harter Secrest & Emery LLP

(57) ABSTRACT

Presented are an apparatus and method for fluid evacuation. An exemplary fluid evacuation system includes a surgical apparatus having a fluid conduit therethrough. The fluid conduit includes a gaseous fluid sorbent material. Additionally, the fluid conduit is fluidly coupled with a vacuum tube fluidly coupled with a vacuum source, wherein the vacuum source is operable to create a flow of fluid through the surgical apparatus fluid conduit and the vacuum tube.

17 Claims, 7 Drawing Sheets

(51) Int. Cl.
  *B01J 20/02*   (2006.01)
  *B01J 20/20*   (2006.01)
  *B01J 20/26*   (2006.01)
  *B01J 20/28*   (2006.01)

(52) U.S. Cl.
  CPC ......... *B01J 20/26* (2013.01); *B01J 20/28026* (2013.01); *A61B 2018/00154* (2013.01); *A61B 2018/00601* (2013.01); *A61B 2018/00607* (2013.01); *A61B 2218/007* (2013.01); *A61B 2218/008* (2013.01)

(56) References Cited

U.S. PATENT DOCUMENTS

| | | | | |
|---|---|---|---|---|
| 5,336,169 | A | * | 8/1994 | Divilio .............. A61B 18/00 604/319 |
| 5,674,219 | A | * | 10/1997 | Monson ............. A61B 18/1402 606/49 |
| 5,874,052 | A | * | 2/1999 | Holland .............. B01D 46/12 422/171 |
| 5,910,291 | A | * | 6/1999 | Skalla ............... B01D 46/106 261/DIG. 26 |
| 5,968,032 | A | * | 10/1999 | Sleister ............... A61B 18/00 606/1 |
| 6,110,259 | A | * | 8/2000 | Schultz .............. B01D 46/10 95/286 |
| 10,561,459 | B2 | | 2/2020 | Fleenor |
| 2002/0128603 | A1 | * | 9/2002 | Booth ............... A61B 17/3421 604/164.01 |
| 2005/0015043 | A1 | * | 1/2005 | Stubbs ............... A61B 17/3423 604/164.01 |
| 2009/0312752 | A1 | * | 12/2009 | Djordjevich .......... A61B 18/20 606/10 |
| 2010/0028397 | A1 | * | 2/2010 | Wooley ............... A01N 25/34 424/649 |
| 2013/0131580 | A1 | | 5/2013 | Blackhurst et al. |
| 2015/0080876 | A1 | | 3/2015 | Worrell et al. |
| 2015/0088133 | A1 | | 3/2015 | Minskoff et al. |
| 2015/0151089 | A1 | | 6/2015 | Tan |
| 2016/0114281 | A1 | | 4/2016 | Bonano et al. |
| 2017/0281255 | A1 | | 10/2017 | Babini et al. |
| 2018/0078301 | A1 | | 3/2018 | Vayser |
| 2019/0388631 | A1 | * | 12/2019 | Silver ................. B01D 46/10 |

FOREIGN PATENT DOCUMENTS

| | | |
|---|---|---|
| CN | 104771803 A | 7/2015 |
| CN | 105228686 A | 1/2016 |
| CN | 107847268 A | 3/2018 |
| CN | 108024824 A | 5/2018 |
| EP | 3684437 A1 | 7/2020 |
| JP | S59-133235 A | 7/1984 |
| JP | H06-506618 A | 7/1994 |
| JP | 2014-057710 A | 4/2014 |
| JP | 2016-123972 A | 7/2016 |
| JP | 2018-140197 A | 9/2018 |
| KR | 10-2014-0144127 A | 12/2014 |
| WO | 2014/204195 A1 | 12/2014 |
| WO | 2017003712 A1 | 1/2017 |

\* cited by examiner

902: providing a surgical apparatus, comprising: an elongated body having a distal end and a proximal end, the elongated body defining a longitudinal axis; a fluid conduit extending through the longitudinal axis of the elongated body, wherein the fluid conduit comprises a porous material impregnated with a gaseous fluid sorbent material; a cutting element disposed adjacent to the distal end; a vacuum source fluidly coupled with the fluid conduit; cutting tissue, whereby a plume develops and is at least partially communicated to the fluid conduit; and sorbing a portion of the plume communicated through the fluid conduit in the gaseous fluid sorbent material.

904: extracting the fluid conduit from the elongated body; and inserting a second fluid conduit comprising a porous material impregnated with a gaseous fluid sorbent material into the elongated body.

FIG. 9

1002: providing a surgical apparatus, comprising an elongated body having a distal end and a proximal end, the elongated body defining a longitudinal axis, a fluid conduit extending through the longitudinal axis of the elongated body, wherein the fluid conduit comprises a biocidal metal, a cutting element disposed adjacent to the distal end, a vacuum source fluidly coupled with the fluid conduit, cutting tissue, whereby a plume develops and is at least partially communicated to the fluid conduit, and at least partially disinfecting the fluid conduit via the biocidal metal 1004: wherein the biocidal metal comprises silver ions 1006: wherein the fluid conduit comprises a porous polymer impregnated with the biocidal metal

FIG. 10

1102: providing an elongated body comprising a distal end and a proximal end, the elongated body defining a longitudinal axis; a fluid conduit extending through the longitudinal axis of the elongated body, wherein the fluid conduit comprises a gaseous fluid sorbent material; a fluid inlet disposed adjacent to the distal end; a cutting element disposed adjacent to the distal end; and a fluid outlet disposed adjacent to the proximal end, wherein the fluid inlet and the fluid outlet are in fluid communication via the fluid conduit 1104: wherein the fluid conduit comprises a porous material impregnated with said gaseous fluid sorbent material 1106: wherein the fluid conduit comprises a porous polymer 1108: wherein the porous polymer comprises a sintered polymer 1110: wherein the gaseous fluid sorbent material comprises activated carbon 1112: wherein the fluid conduit comprises a tube operable to be removed from the elongated body 1114: wherein the tube comprises a slot operable to accommodate the cutting element during removal of the tube from the elongated body 1116: wherein the fluid conduit comprises a tube having a radially inner surface, a sorbent material coupled with the radially inner surface of the tube, and a permeable polymer coupled with a radially inner surface of the sorbent material 1118: wherein the fluid conduit comprises a plurality of axially spaced rings of the sorbent material

FIG. 11

FILTERING METHOD AND APPARATUS

BACKGROUND OF THE INVENTION

Field of the Invention

The present disclosure relates generally to fluid evacuation and more specifically to smoke evacuation and filtering capabilities during medical procedures.

Description of Related Art

Toxic or otherwise harmful surgical smoke and aerosol, or plume, may be produced during surgery. For example, when surgical energy is delivered to a cell, heat may be created causing vaporization of intracellular fluid. Vaporizing intracellular fluid increases the pressure inside the effected cell, eventually causing the cell membrane to rupture. A plume of smoke containing water vapor is released into the atmosphere of the operating room or doctor's office. At the same time, the heat created by the surgical energy may char the protein and other organic matter within the cell and may cause thermal necrosis in adjacent cells. The charring of cells may also release harmful contaminants, such as carbonized cell fragments and gaseous hydrocarbons.

BRIEF SUMMARY OF THE INVENTION

In view of the foregoing, it is an object of the present disclosure to provide a method and apparatus for surgical procedures.

A first exemplary embodiment of the present disclosure provides a surgical apparatus. The surgical apparatus includes an elongated body comprising a distal end and a proximal end, the elongated body defining a longitudinal axis, and a fluid conduit extending through the longitudinal axis of the elongated body, wherein the fluid conduit comprises a gaseous fluid sorbent material. The surgical apparatus further includes a fluid inlet disposed adjacent to the distal end, and a cutting element disposed adjacent to the distal end. The surgical apparatus still further includes a fluid outlet disposed adjacent to the proximal end, wherein the fluid inlet and the fluid outlet are in fluid communication via the fluid conduit.

A second exemplary embodiment of the present disclosure presents a surgical apparatus. The surgical apparatus an elongated body comprising a distal end and a proximal end, the elongated body defining a longitudinal axis, and a fluid conduit extending through the longitudinal axis of the elongated body, wherein the fluid conduit comprises a biocidal metal. The surgical apparatus further includes a fluid inlet disposed adjacent to the distal end. The surgical apparatus still further includes a cutting element disposed adjacent to the distal end, and a fluid outlet disposed adjacent to the proximal end, wherein the fluid inlet and the fluid outlet are in fluid communication via the fluid conduit.

A third exemplary embodiment of the present disclosure presents a method. The method includes providing a surgical apparatus, comprising: an elongated body having a distal end and a proximal end, the elongated body defining a longitudinal axis, a fluid conduit extending through the longitudinal axis of the elongated body, wherein the fluid conduit comprises a porous material impregnated with a gaseous fluid sorbent material, a cutting element disposed adjacent to the distal end, a vacuum source fluidly coupled with the fluid conduit, cutting tissue, whereby a plume develops and is at least partially communicated to the fluid conduit, and sorbing a portion of the plume communicated through the fluid conduit in the gaseous fluid sorbent material.

A fourth exemplary embodiment of the present disclosure presents a method. The method includes providing a surgical apparatus, comprising an elongated body having a distal end and a proximal end, the elongated body defining a longitudinal axis, a fluid conduit extending through the longitudinal axis of the elongated body, wherein the fluid conduit comprises a biocidal metal, a cutting element disposed adjacent to the distal end, a vacuum source fluidly coupled with the fluid conduit, cutting tissue, whereby a plume develops and is at least partially communicated to the fluid conduit, and at least partially disinfecting the fluid conduit via the biocidal metal.

The following will describe embodiments of the present disclosure, but it should be appreciated that the present disclosure is not limited to the described embodiments and various modifications of the disclosure are possible without departing from the basic principle. The scope of the present disclosure is therefore to be determined solely by the appended claims.

BRIEF DESCRIPTION OF THE SEVERAL VIEWS OF THE DRAWINGS

The accompanying drawings are incorporated herein as part of the specification. The drawings described herein illustrate embodiments of the presently disclosed subject matter and are illustrative of selected principles and teachings of the present disclosure. However, the drawings do not illustrate all possible implementations of the presently disclosed subject matter and are not intended to limit the scope of the present disclosure in any way.

FIG. 9 presents a logic flow diagram suitable for practicing exemplary embodiments of the present disclosure.

FIG. 10 presents another logic flow diagram suitable for practicing exemplary embodiments of the present disclosure.

FIG. 11 presents yet another logic flow diagram suitable for practicing exemplary embodiments of the present disclosure.

DETAILED DESCRIPTION OF THE INVENTION

Figure 1:
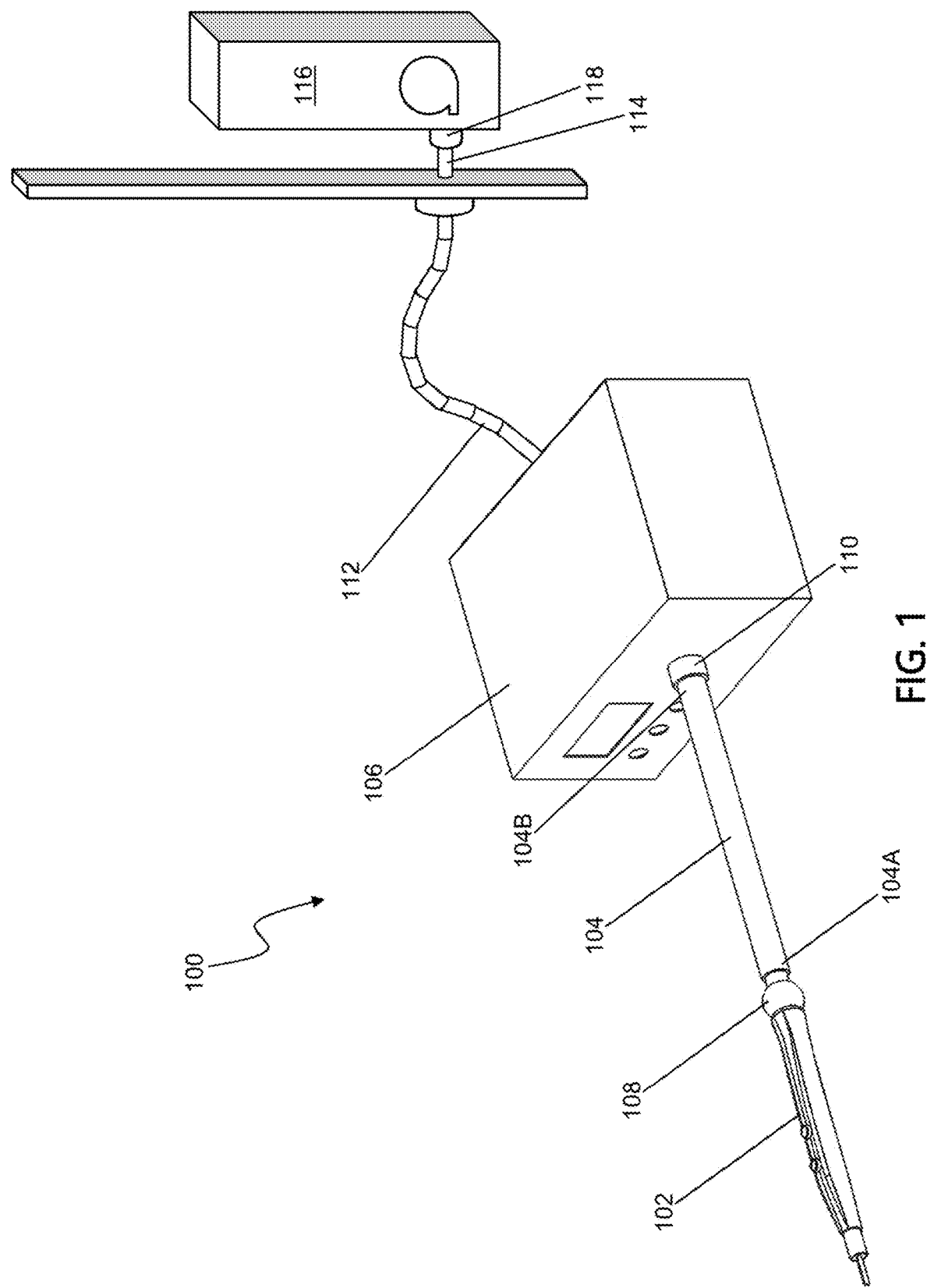
FIG. 1 illustrates a schematic of an exemplary evacuation system according to an embodiment of the present disclosure.

It is to be understood that the invention may assume various alternative orientations and step sequences, except where expressly specified to the contrary. It is also to be understood that the specific assemblies and systems illustrated in the attached drawings and described in the following specification are simply exemplary embodiments of the inventive concepts defined herein. Hence, specific dimensions, directions, or other physical characteristics relating to the embodiments disclosed are not to be considered as limiting, unless expressly stated otherwise. Also, although they may not be, like elements in various embodiments described herein may be commonly referred to with like reference numerals within this section of the application.

There remains a need for a fluid evacuation system capable of efficiently and effectively filtering at least a portion of the plume created during surgery. As such, embodiments of the present disclosure provide a method and apparatus for filtering gas, fluid and/or particulates. Embodiments of the present disclosure include a surgical apparatus having a conduit maintaining a material operable to sorb (e.g., absorb or adsorb) gas, fluid, and/or particulates that pass through the conduit.

As illustrated in FIG. 1, in an embodiment, an evacuation system 100 (also referred to as a fluid evacuation system) may comprise a surgical apparatus 102 in fluid communication with a filter assembly 106 via a first tube 104. A first end 104A of the first tube 104 may be in sealed connection with a proximal end 108 of the surgical apparatus 102, and a second end 104B of the first tube 104 may be in sealed connection with a fluid inlet 110 of the filter assembly 106. It should be appreciated that embodiments of the first tube 104 may be either removeably or fixedly attached to the surgical apparatus proximal end 108 and filter assembly fluid inlet 110. A second tube 112 may comprise a first end in sealed connection with a fluid outlet of the filter assembly 106 and a second end 114 in sealed connection with a fluid inlet 118 of a vacuum power unit 116. Embodiments of the second tube 112 include second tube 112 being removeably or fixedly attached with fluid inlet 118 and fluid outlet 114. In an embodiment, as illustrated in FIG. 1, the vacuum power source 116 may be a central vacuum unit installed in a wall of medical facility. In another embodiment, the vacuum power source 116 may be a standalone, or remote, vacuum unit located adjacent to or spaced apart from the filter assembly 106. In still another embodiment, the vacuum power source 116 and the filter assembly 106 may be integrated into a single housing. The vacuum power source 116 is operable to create or urge a fluid flow through the surgical apparatus 102, the first tube 104, the filter assembly 106, and the second tube 112.

It should be appreciated that embodiments of the present disclosure include surgical apparatus 102 being directly and fluidly connected to vacuum power source 116. In other words, embodiments includes there being no filter assembly 106 being located intermediate surgical apparatus 102 and vacuum power source 116. In this alternative embodiment second tube 112 is directly and fluidly connected to first tube 104 or first end 104A.

Figure 2:
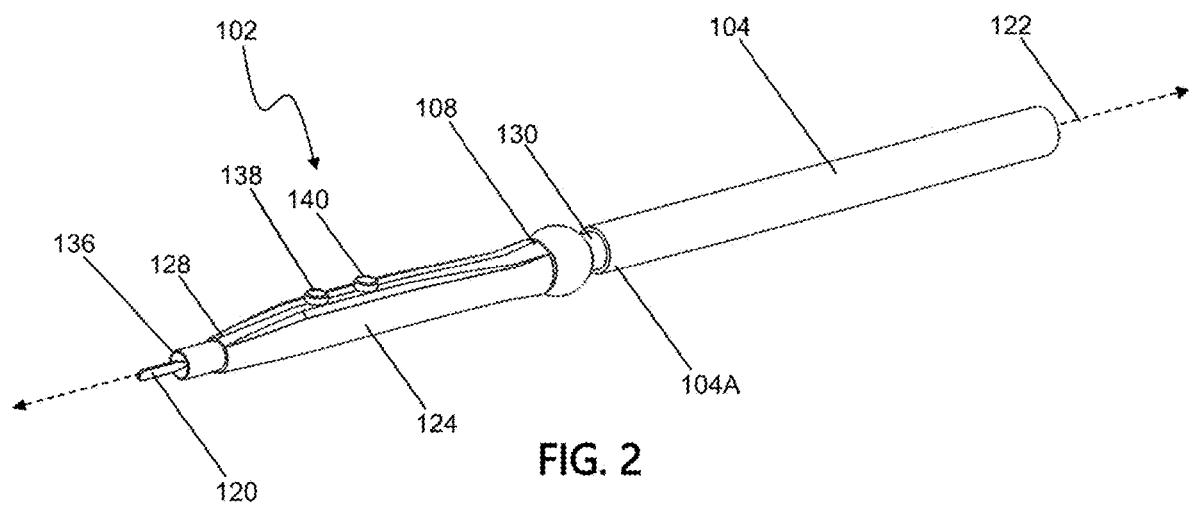
FIG. 2 illustrates an exemplary surgical apparatus according to an embodiment of the present disclosure.

As illustrated in FIG. 2, in an embodiment, the surgical apparatus 102 may include an electrosurgical pencil having a cutting element 120 and a longitudinal axis 122. The surgical apparatus 102 may also comprise a hollow body 124 enclosing a fluid conduit 126 (see FIG. 3). In an embodiment, the fluid conduit 126 may extend coaxially through the longitudinal axis 122 of the electrosurgical pencil hollow body 124 from a distal end 128 to the proximal end 108 thereof. As illustrated in FIG. 2, the cutting element 120 may be disposed at the distal end 128 of the electrosurgical pencil hollow body 124.

With continued reference to FIG. 2, in an embodiment, the cutting element 120 may comprise at least one electrode. The at least one electrode 120 may be employed to apply an electrical current to a patient's tissue for cutting and/or coagulation thereof In other embodiments, not depicted, the cutting element 120 may comprise, but is not limited to, an ultrasonic scalpel or a laser scalpel.

Figure 3:
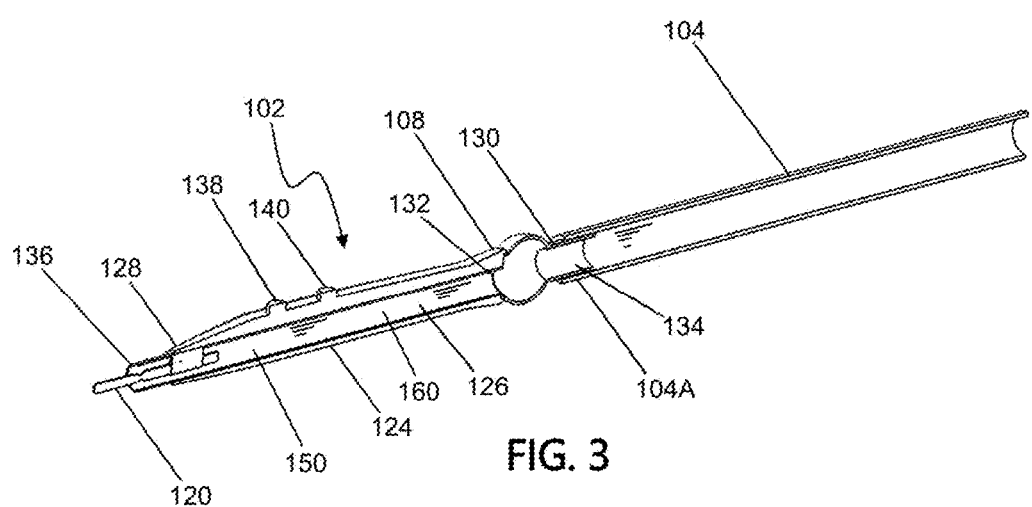
FIG. 3 illustrates a cross sectional view of an exemplary surgical apparatus according to an embodiment of the present disclosure.

As illustrated in FIG. 3, a port 132 may be disposed in the proximal end 108 of the electrosurgical pencil hollow body 124 in fluid communication with the fluid conduit 126. In an embodiment, a fitting 130 located at the electrosurgical pencil proximal end 108 may comprise a barbed fitting having a fluid conduit 134 disposed therethrough. The fitting 130 is coupled with the electrosurgical pencil proximal end 108 and is in fluid communication with port 132. In other embodiments, the fitting 130 may comprise a connector of other designs. For example, a female connector may be utilized in place of the barbed fitting 130. A female connector may be utilized to keep the inner diameter of the fitting, and hence the fluid conduit 134, as large as possible.

As illustrated in FIGS. 2 and 3, the electrosurgical pencil distal end 128 may be provided with an inlet 136 in fluid communication with the hollow body fluid conduit 126. During operation of the surgical apparatus 102, vacuum power source 116 urges or creates a flow of gas, fluid, and/or particulates (e.g., surgical smoke) generated by cutting element 120 to enter the hollow body inlet 136 and passes through the fluid conduit 126 to the port 132. From the port 132, the gas, fluid, and/or particulates flows through the fitting 130 to the tube 104. Accordingly, gas, fluid, and/or particulates from a procedure may be conveyed through the surgical apparatus 102 to the tube 104. From the tube 104, the gas, fluid, and/or particulates are conveyed to the filter assembly 106 or directly to vacuum power source 116 for the embodiment in which filter assembly 106 is not present. The term surgical smoke may be referred to herein interchangeably with the term plume. It should be appreciated that while embodiments of the present disclosure may be described as being operable to evacuate gas, fluid, particulates, smoke and/or plume, embodiments are also operable to evacuate smoke and/or plume.

With continued reference to FIGS. 2 and 3, in an embodiment, the surgical apparatus 102 may be provided with a cut button 138 and a coagulate button 140 that provide different levels of current to the cutting element electrode 120. In one embodiment, the cut button 138 is operable to activate the cutting element electrode 120 at a first power level and the coagulate button 140 is operable to activate the cutting element electrode 120 at a second power level. In an embodiment, the first power level may be higher than the second power level.

As illustrated in FIG. 3, in an embodiment, the surgical apparatus fluid conduit 126 may include a sorbent material 150 operable to adsorb or absorb at least a portion of the surgical smoke (e.g., gas, fluid, and/or particulates) that passes through fluid conduit 126. The sorbent material 150 may be uniformly distributed through the inner radial surface of fluid conduit 126 in one embodiment, it may be concentrated in one or more areas of the inner radial surface of fluid conduit 126, or it may be concentrated within fluid conduit 126 adjacent the inner radial surface. Embodiments include the entire inner radial surface 502 of fluid conduit 126 along the longitudinal axis 122 including a sorbent material 150. Embodiments also include the sorbent material 150 being located in multiple locations in the radial and longitudinal directions on the inner radial surface 502 of fluid conduit 126 such portions of the inner radial surface 502 of fluid conduit 126 include the sorbent material 150 and other portions of the inner radial surface 502 of fluid conduit 126 do not include the sorbent material 150.

Figure 4:
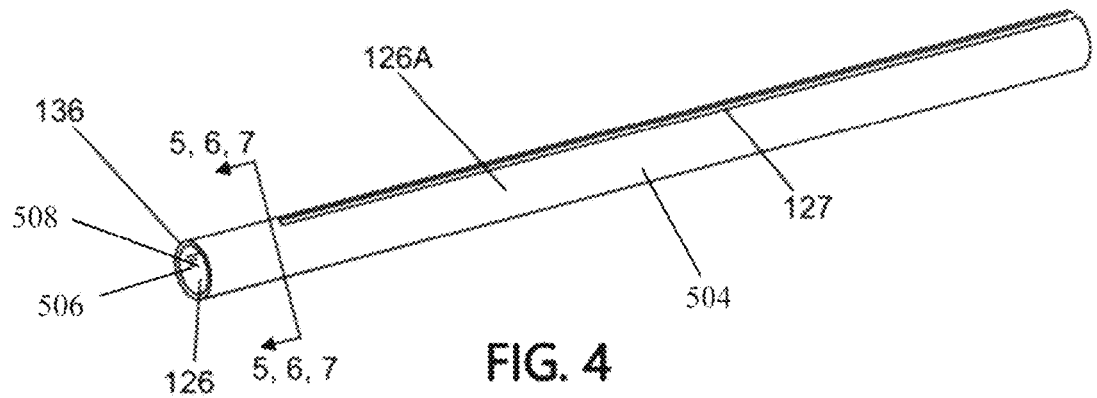
FIG. 4 illustrates a portion of an exemplary surgical apparatus according to an embodiment of the present disclosure.

As illustrated in FIG. 4, in an embodiment, the fluid conduit 126 may comprise or maintain a tube 126A. The tube 126A may be a replaceable component of the surgical apparatus 102. Embodiments of tube 126A have an outer diameter less than the inner diameter of the fluid conduit 126 such that the outer radial surface 504 of tube 126A and the inner radial surface 502 of the fluid conduit 126 form a friction fit that allows tube 126A to be removeable from surgical apparatus 102. Tube 126A includes a hollow passageway 508 defined by its inner radial surface 502. The hollow passageway 508 of tube 126A is fluidly connected to the fluid conduit 126 when tube 126A is located within fluid conduit 126 of surgical apparatus 102. After one or a plurality of uses of the surgical apparatus 102, the tube 126A may be removed from the surgical apparatus 102 and replaced with a new tube 126A to ensure the efficacy of the sorbent material 150. In an embodiment, the tube 126A may define a slot 127 extending through the long axis of tube 126A for accommodating the cutting element electrode 120 during removal and insertion of the tube 126A.

Figure 5:
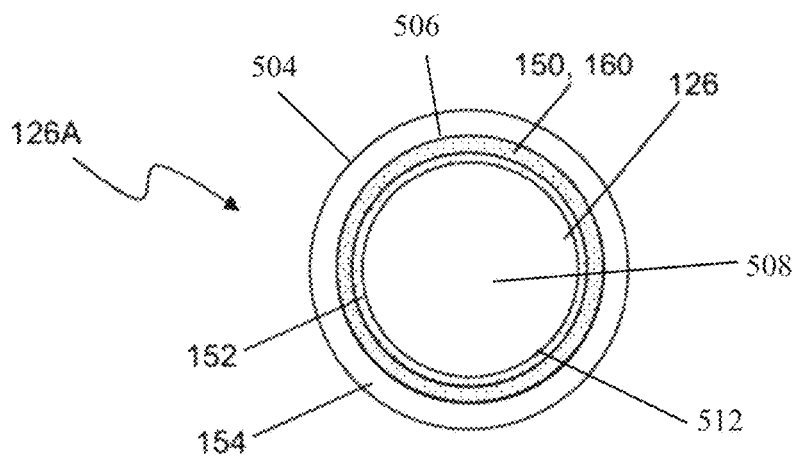
FIG. 5 illustrates a cross sectional view of a portion an exemplary surgical apparatus according to an embodiment of the present disclosure.

As illustrated in FIG. 5, in an embodiment, the tube 126A may comprise a generally right circular hollow cylinder 154 formed of, for example, a polymeric material. A layer of sorbent material 150 may be coupled to the radially inward surface 506 of the hollow cylinder 154, and a layer of a permeable polymer 152 may be coupled to a radially inward surface 510 of the sorbent material 150. In this embodiment, hollow cylinder 154, sorbent material 150, and permeable polymer 152 form concentric elements and the inner radial surface 512 of the permeable polymer 152 define the hollow passageway 508. The sorbent material 150 may extend through the long axis of the hollow cylinder 154 or may be located along one or more portions of the hollow cylinder 154.

Figure 6:
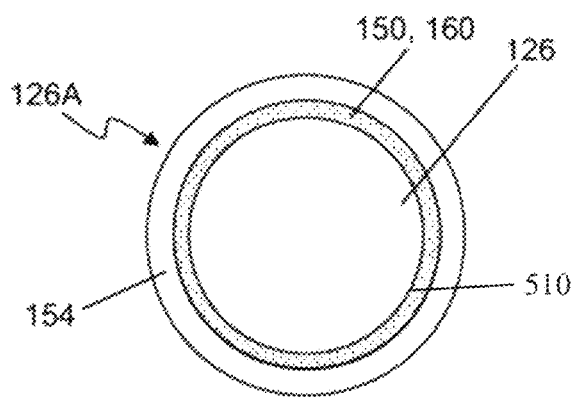
FIG. 6 illustrates a cross sectional view of a portion an exemplary surgical apparatus according to another embodiment of the present disclosure.

As illustrated in FIG. 6, in an embodiment, the sorbent material 150 may define the fluid conduit 126 without having the permeable polymer 152. In other words, embodiments include the inner radial surface 502 of tube 126A having a layer of sorbent material 150 alone such that the hollow passageway 508 is defined by the inner radial surface 510 of the sorbent material 150.

Figure 7:
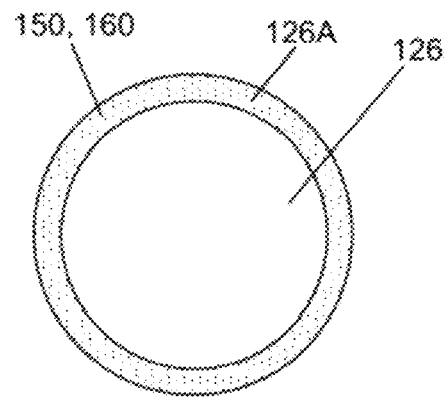
FIG. 7 illustrates a cross sectional view of a portion an exemplary surgical apparatus according to still another embodiment of the present disclosure.

As illustrated in FIG. 7, in another embodiment, the tube 126A may be formed of a porous polymer and impregnated with a sorbent material 150 such as, but not limited to, activated carbon. The sorbent material 150 may also be, but is not limited to, a porous polymer such as a conjugated microporous polymer or a sintered polymer.

Figure 8:
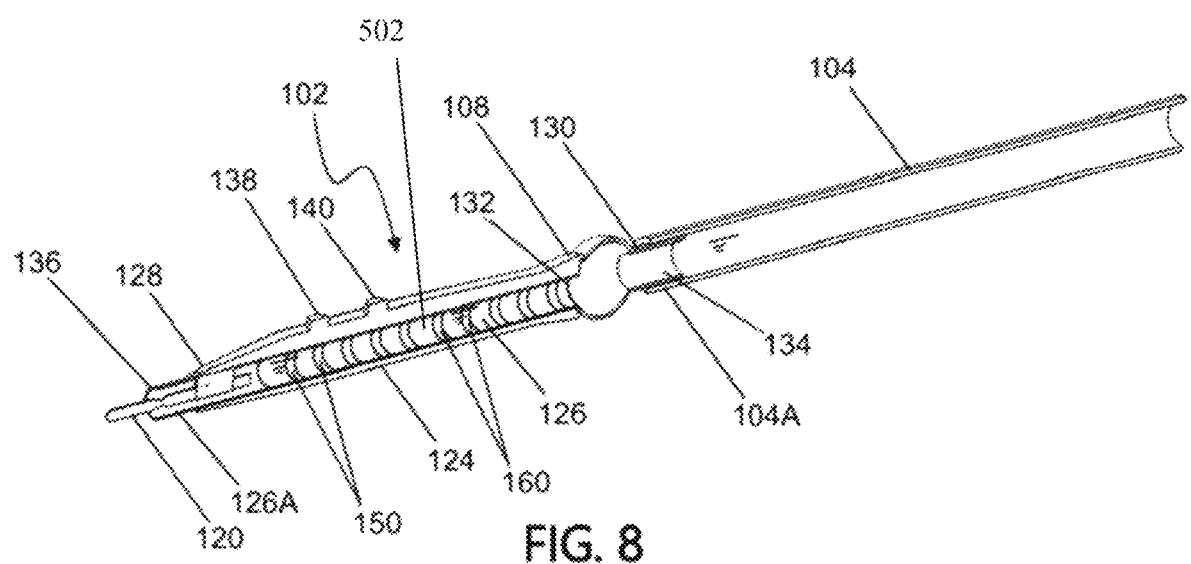
FIG. 8 illustrates a cross sectional view of an exemplary surgical apparatus according to an embodiment of the present disclosure.

As illustrated in FIG. 8, in an embodiment, the sorbent material 150 may form a plurality of rings or hollow cylinders coupled with the tube 126A. The rings of sorbent material 150 may be coupled with the tube 126A via an adhesive, a press fit, or an over-molding process, but are not limited to such processes. In another embodiment, the tube 126A may define generally annular recesses in the radially inner surface thereof in which the rings of sorbent material 150 are located. In yet another embodiment, the rings of sorbent material 150 may project into the fluid conduit 126 to create areas of turbulent and/or recirculating flow to increase the volume and/or duration of contact between the surgical smoke and the sorbent material 150.

During operation of the surgical apparatus 102, gas, fluid, and/or particulates are drawn through the fluid conduit 126. A portion of gas, fluid, and/or particulates is adsorbed and/or absorbed by the sorbent material 150. In an embodiment, where the sorbent material 150 is an adsorbent, a portion of the molecules, atoms, and/or ions of the surgical smoke adhere to the sorbent material 150. A portion of the surgical smoke is thereby filtered from the flow of surgical smoke through the evacuation system 100. The evacuation system 100 may include additional filters, including but not limited to particulate filters, downstream of the surgical apparatus 102. By utilizing the surgical apparatus 102 having a fluid conduit 126 with integrated sorbent material 150, the evacuation system 100 maintains increased filtering capacity without decreasing a flow rate of the surgical smoke through the evacuation system 100.

Referring now to FIGS. 3-8, the surgical apparatus fluid conduit 126 may include a biocidal material 160 in place of, or in addition to, the sorbent material 150. The biocidal material 160 may be, but is not limited to, biocidal metal. The biocidal metal may comprise silver ions. Utilizing the surgical apparatus 102 having a fluid conduit 126 with integrated biocidal material 160 militates against the development of microbes within the fluid conduit 126. Preventing the development of microbes within the fluid conduit 126 may extend the lifespan of the tube 126A and reduce the frequency with which the tube 126A should be replaced.

It should be appreciated that embodiments of the present disclosure provide a surgical apparatus that includes a conduit that maintains a material operable to absorb or adsorb gas, fluid, and/or particulates that pass through the conduit. In each embodiment, the material that is operable to adsorb or absorb fails to obstruct the flow through the conduit. In this regard, the material does not substantially decrease the area of flow of the conduit nor does it directly obstruct the flow of gas, fluid, and/or particulates through the conduit. Rather embodiments of the present disclosure provide a surgical apparatus that collects and/or filters gas, fluid, and/or particulates simply by having the gas, fluid and/or particulates pass through the conduit. Embodiments of the present disclosure therefore advantageously allow an evacuator to urge a flow through the conduit without having to overcome obstructions from traditional filters.

Reference is now made to FIG. 9, which depicts a logic flow diagram suitable for practicing exemplary embodiments of the present disclosure. Block 902 specifies providing a surgical apparatus, comprising: an elongated body having a distal end and a proximal end, the elongated body defining a longitudinal axis; a fluid conduit extending through the longitudinal axis of the elongated body, wherein the fluid conduit comprises a porous material impregnated with a gaseous fluid sorbent material; a cutting element disposed adjacent to the distal end; a vacuum source fluidly coupled with the fluid conduit; cutting tissue, whereby a plume develops and is at least partially communicated to the fluid conduit; and sorbing a portion of the plume communicated through the fluid conduit in the gaseous fluid sorbent material. The process continues at block 904 which states extracting the fluid conduit from the elongated body; and inserting a second fluid conduit comprising a porous material impregnated with a gaseous fluid sorbent material into the elongated body.

Referring to FIG. 10, shown is another logic flow diagram suitable for practicing exemplary embodiments of the present disclosure. Block 1002 states providing a surgical apparatus, comprising an elongated body having a distal end and a proximal end, the elongated body defining a longitudinal axis, a fluid conduit extending through the longitudinal axis of the elongated body, wherein the fluid conduit comprises a biocidal metal, a cutting element disposed adjacent to the distal end, a vacuum source fluidly coupled with the fluid conduit, cutting tissue, whereby a plume develops and is at least partially communicated to the fluid conduit, and at least partially disinfecting the fluid conduit via the biocidal metal. Then block 1004 specifies wherein the biocidal metal comprises silver ions. Finally, block 1006 recites wherein the fluid conduit comprises a porous polymer impregnated with the biocidal metal.

Referring to FIG. 11, shown is yet another logic flow diagram suitable for practicing exemplary embodiments of the present disclosure. Beginning at block 1102, it states providing an elongated body comprising a distal end and a proximal end, the elongated body defining a longitudinal axis; a fluid conduit extending through the longitudinal axis of the elongated body, wherein the fluid conduit comprises a gaseous fluid sorbent material; a fluid inlet disposed adjacent to the distal end; a cutting element disposed adjacent to the distal end; and a fluid outlet disposed adjacent to the proximal end, wherein the fluid inlet and the fluid outlet are in fluid communication via the fluid conduit. Block 1104 then specifies wherein the fluid conduit comprises a porous material impregnated with said gaseous fluid sorbent material.

Following block 1104, block 1106 states wherein the fluid conduit comprises a porous polymer. Block 1108 then recites wherein the porous polymer comprises a sintered polymer. Block 1110 specifies wherein the gaseous fluid sorbent material comprises activated carbon. Next block 1112 states wherein the fluid conduit comprises a tube operable to be removed from the elongated body. Block 1114 states wherein the tube comprises a slot operable to accommodate the cutting element during removal of the tube from the elongated body. Block 1116 relates to wherein the fluid conduit comprises a tube having a radially inner surface, a sorbent material coupled with the radially inner surface of the tube, and a permeable polymer coupled with a radially inner surface of the sorbent material. Finally, block 1118 recites wherein the fluid conduit comprises a plurality of axially spaced rings of the sorbent material.

The logic flow diagrams of FIGS. 9, 10 and 11 may be considered to illustrate the operation of a method of using exemplary embodiments disclosed herein or the specific manner in which components of a device are configured to cause the device to operate.

One or more features of the embodiments described herein may be combined to create additional embodiments which are not depicted. While various embodiments have been described in detail above, it should be understood that they have been presented by way of example, and not limitation. It will be apparent to persons skilled in the relevant arts that the disclosed subject matter may be embodied in other specific forms, variations, and modifications without departing from the scope, spirit, or essential characteristics thereof. The embodiments described above are therefore to be considered in all respects as illustrative, and not restrictive. The scope of the invention is indicated by the appended claims, and all changes that come within the meaning and range of equivalents thereof are intended to be embraced therein.

The invention claimed is:

1. A surgical apparatus, comprising:
   an elongated body comprising a distal end and a proximal end, the elongated body defining a longitudinal axis;
   a hollow fluid conduit extending through the longitudinal axis of the elongated body, wherein the fluid conduit comprises a gaseous fluid sorbent material uniformly distributed through an entire inner radial surface of the hollow fluid conduit from the distal end to the proximal end;
   a fluid inlet disposed adjacent to the distal end;
   a cutting element disposed adjacent to the distal end and adjacent the gaseous fluid sorbent material; and
   a fluid outlet disposed adjacent to the proximal end, wherein the fluid inlet and the fluid outlet are in fluid communication via the fluid conduit.

2. The surgical apparatus according to claim 1, wherein the fluid conduit comprises a porous material impregnated with the gaseous fluid sorbent material.

3. The surgical apparatus according to claim 1, wherein the fluid conduit comprises a porous polymer.

4. The surgical apparatus according to claim 3, wherein the porous polymer comprises a sintered polymer.

5. The surgical apparatus according to claim 1, wherein the gaseous fluid sorbent material comprises activated carbon.

6. The surgical apparatus according to claim 1, wherein the fluid conduit comprises a tube operable to be removed from the elongated body.

7. The surgical apparatus according to claim 6, wherein the tube comprises a slot operable to accommodate the cutting element during removal of the tube from the elongated body.

8. The surgical apparatus according to claim 1, wherein the gaseous fluid sorbent material is adsorbent.

9. The surgical apparatus according to claim 1, wherein:
   the fluid conduit comprises a tube including a radially inner surface;
   the gaseous fluid sorbent material is coupled with the radially inner surface of the tube; and
   a permeable polymer is coupled with a radially inner surface of the sorbent material.

10. The surgical apparatus according to claim 1, wherein the cutting element comprises an electrode extending from the distal end.

11. The surgical apparatus according to claim 1, the apparatus further comprising:
    a vacuum tube fluidly coupled with the fluid conduit; and
    a vacuum source fluidly coupled with the vacuum tube, the vacuum source operable to create a flow of fluid.

12. The surgical apparatus according to claim 1, wherein the fluid conduit comprises a biocidal metal.

13. A surgical apparatus, comprising:
    an elongated body comprising a distal end and a proximal end, the elongated body defining a longitudinal axis;
    a hollow fluid conduit extending through the longitudinal axis of the elongated body, wherein the fluid conduit comprises a plurality of biocidal metal spaced apart rings located on an inner radial surface of the hollow fluid conduit and arranged axially between the distal end and the proximal end;
    a fluid inlet disposed adjacent to the distal end;
    a cutting element disposed adjacent to the distal end and arranged at least partially within the hollow fluid conduit axially between the distal end and the proximal end; and
    a fluid outlet disposed adjacent to the proximal end, wherein the fluid inlet and the fluid outlet are in fluid communication via the fluid conduit.

14. The surgical apparatus according to claim 13, wherein the biocidal metal comprises silver ions.

15. The surgical apparatus according to claim 13, wherein the plurality of biocidal metal spaced apart rings comprise a porous polymer impregnated with biocidal metal.

16. A method of surgical operation, the method comprising:
- providing a surgical apparatus, comprising:
  - an elongated body having a distal end and a proximal end, the elongated body defining a longitudinal axis;
  - a first tube removably arranged within and at least partially axially aligned with the elongated body, wherein the first tube comprises a porous material impregnated with a gaseous fluid sorbent material distributed through a portion of an inner radial surface of the first tube;
  - a cutting element disposed adjacent to a first end of the first tube; and
  - a vacuum source fluidly coupled with a second end of the first tube;
- cutting tissue, whereby a plume develops and is at least partially communicated to the first tube; and
- sorbing a portion of the plume communicated through the first tube in the gaseous fluid sorbent material.

17. The method of surgical operation according to claim 16, the method further comprising:
- removing the first tube from the elongated body; and
- inserting a second tube comprising a porous material impregnated with a gaseous fluid sorbent material into the elongated body.

* * * * *